US008148165B2

(12) United States Patent
Nakano

(10) Patent No.: US 8,148,165 B2
(45) Date of Patent: Apr. 3, 2012

(54) APPARATUS AND METHOD FOR MEASURING CONCENTRATION OF CARBON DIOXIDE IN WATER

(75) Inventor: Yoshiyuki Nakano, Kanagawa (JP)

(73) Assignee: Japan Agency for Marine-Earth Science and Technology, Yokosuka-shi (JP)

( * ) Notice: Subject to any disclaimer, the term of this patent is extended or adjusted under 35 U.S.C. 154(b) by 35 days.

(21) Appl. No.: 12/681,030

(22) PCT Filed: Dec. 22, 2008

(86) PCT No.: PCT/JP2008/073333
§ 371 (c)(1),
(2), (4) Date: Mar. 31, 2010

(87) PCT Pub. No.: WO2009/093401
PCT Pub. Date: Jul. 30, 2009

(65) Prior Publication Data
US 2010/0240141 A1    Sep. 23, 2010

(30) Foreign Application Priority Data

Jan. 25, 2008  (JP) .................................. 2008-015517
Nov. 12, 2008  (JP) .................................. 2008-289353

(51) Int. Cl.
*G01N 31/22* (2006.01)
*G01N 21/31* (2006.01)
(52) U.S. Cl. .................. 436/163; 422/82.09; 422/82.05; 422/68.1; 422/50

(58) Field of Classification Search .................. 436/163; 422/82.09, 82.05, 68.1, 50
See application file for complete search history.

(56) References Cited

FOREIGN PATENT DOCUMENTS

| JP | 01-165938 | 6/1989 |
|---|---|---|
| JP | 05-005736 | 1/1993 |
| JP | 08-505218 | 6/1996 |
| JP | 2002-514758 | 5/2002 |
| WO | 9320431 | 10/1993 |
| WO | 9958961 | 11/1999 |

OTHER PUBLICATIONS

PCT/JP2008/073333 International Search Report, 2009, pp. 1-2.*
Yoshiyuki Nakano, et al., "Simultaneous Vertical Measurements of In Situ pH and CO2 in the Sea Using Spectrophotometric Profilers", Journal of Oceanography, vol. 62, pp. 71 to 81.

* cited by examiner

*Primary Examiner* — Christine T Mui
(74) *Attorney, Agent, or Firm* — Rankin, Hill & Clark LLP

(57) ABSTRACT

An apparatus for measuring the concentration of carbon dioxide in water that can correct a reduction in measurement accuracy based on deterioration of a pH indicator is provided. A carbon dioxide concentration measurement apparatus includes a deterioration determining section that measures a change rate $\Delta A_0$ of an isosbestic point absorbance $A_0$ and determines that the pH indicator solution is deteriorated when the change rate $\Delta A_0$ is reduced by a predetermined reduction rate or more. After the deterioration determining section determines deterioration of the pH indicator solution, a pH value computing section computes the pH value of the pH indicator solution using a corrected pH computation expression for correcting a deterioration of the pH value of the pH indicator solution on the basis of the change rate $\Delta A_0$ of the isosbestic point absorbance $A_0$.

21 Claims, 9 Drawing Sheets

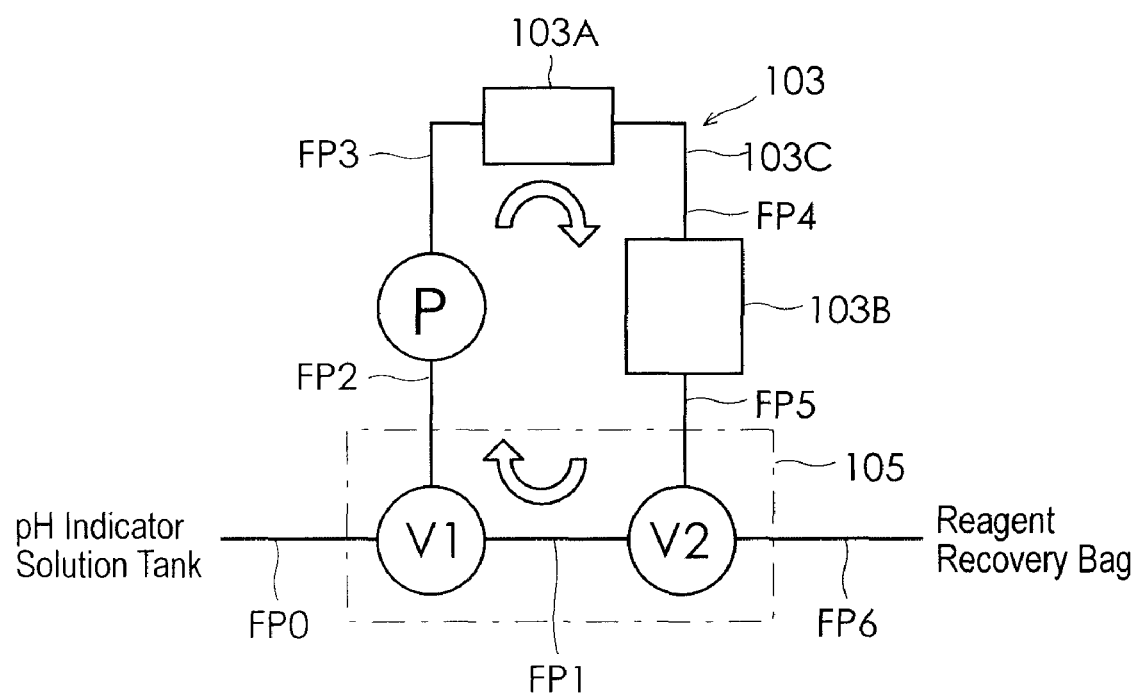

APPARATUS AND METHOD FOR MEASURING CONCENTRATION OF CARBON DIOXIDE IN WATER

TECHNICAL FIELD

The present invention relates an apparatus and a method for measuring the concentration of carbon dioxide in water on the basis of the absorbance of a pH indicator solution filling a measurement cell.

BACKGROUND ART

Japanese Unexamined Patent Application Publication No. Hei 08-505218 "Method and Apparatus for Measuring Concentration of Carbon Dioxide Dissolved in Seawater" (Patent Document 1) discloses a technique in which a peak absorption wavelength $\lambda_M$, a wavelength $\lambda_B$ at which dye does not absorb light, and a wavelength $\lambda_I$ close to the isosbestic point of the dye are measured from a light absorption spectrum, the carbon dioxide concentration is measured at only one wavelength $\lambda_M$ with absorption peak and corrected at $\lambda_B$ at which the dye does not absorb light, and the stability of the indicator is evaluated on the basis of measurement at the wavelength $\lambda_I$ close to the isosbestic point of the dye.

Japanese Unexamined Patent Application Publication No. 2002-514758 "System and Method for Optical Chemical Detection" (Patent Document 2) discloses a technique in which the intensities of first and second output light are measured to determine the concentration of an analysis subject (carbon dioxide: $CO_2$).

A paper titled "Simultaneous Vertical Measurements of In Situ pH and $CO_2$ in the Sea Using Spectrophotometric Profilers" (Non-Patent Document 1) presented by the present inventor in the Journal of Oceanography, Vol. 62, pp. 71 to 81, 2006 proposes a method for measuring the concentration of carbon dioxide in seawater as described below. A pH indicator solution changes in color in accordance with changes in pH, the pH indicator solution having a carbon dioxide concentration that finally becomes equal to the concentration of carbon dioxide in water, and the pH indicator solution establishes an equilibrium of:

  [Chemical formula 1]

if the pH indicator solution is represented as $H_2L$.

First, an absorption spectrum of light absorbed by the pH indicator solution is measured. Next, a first absorbance $A_1$ at a first peak absorption wavelength $\lambda_1$ which is equivalent to a concentration of $HL^-$ in the pH indicator solution, a second absorbance $A_2$ at a second peak absorption wavelength $\lambda_2$ which is equivalent to a concentration of $L^{2-}$ which determines a pH, an isosbestic point absorbance $A_0$ at an isosbestic point wavelength at which the pH indicator solution does not show changes in absorbance in accordance with changes in pH, and a non-light-absorbing absorbance $A_b$ at a non-light-absorbing wavelength $\lambda_b$ are computed from the absorption spectrum. Then, a pH value of the pH indicator solution is computed using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$. Finally, the concentration of carbon dioxide in water is determined from the computed pH value.

[Patent Document 1] Japanese Unexamined Patent Application Publication No. Hei 08-505218

[Patent Document 2] Japanese Unexamined Patent Application Publication No. 2002-514758

[Non-Patent Document 1] Journal of Oceanography, Vol. 62, pp. 71 to 81, 2006, "Simultaneous Vertical Measurements of In Situ kpH and $CO_2$ in the Sea Using Spectrophotometric Profilers"

DISCLOSURE OF INVENTION

Problem to be Solved by the Invention

Even if the carbon dioxide concentration is corrected at $\lambda_B$ at which the dye does not absorb light as in the technique disclosed in Patent Document 1, however, the carbon dioxide concentration is easily affected by the noise of a detector. Also, the measurement according to the technique is a relative measurement which inevitably requires a standard substance. From a description that thymol blue, which is as the pH indicator used as the dye, has only an ignorable absorbance in the acid form at $\lambda_M$, it is understood that measurement can be performed at only one wavelength, namely the peak wavelength $\lambda_M$. However, measurement cannot be performed with a pH indicator whose basic spectrum and acid spectrum overlap each other, and thus indicators that can be used in the technique are limited. In the technique, further, the stability of the indicator is evaluated on the basis of measurement at the wavelength close to the isosbestic point. However, the influence of the deteriorated indicator on the absorbance at the absorption peak wavelength is not considered. If a new substance generated by decomposition of the indicator absorbs an unignorable amount light at the absorption peak wavelength $\lambda_M$, it may be difficult to correct the carbon dioxide concentration on the basis of only measurement at $\lambda_M$. Moreover, if light becomes weak due to a voltage drop, light may be attenuated significantly, and thus measurement at only the absorption peak wavelength $\lambda_M$ may result in unstable measurement values. Furthermore, "the distribution of experiment points around the calibration curve is 1%" according to Patent Document 1, and thus the accuracy of repeated measurements is low.

In the technique disclosed in Patent Document 2, the intensities of first and second output light are measured to determine the concentration of an analysis subject. However, the light to be measured is excitation light, and thus the measurement accuracy is about one digit lower than the measurement accuracy obtained if the absorbance is theoretically measured.

In order to address such issues of the related art, in the technique for measuring the carbon dioxide concentration according to Non-Patent Document 1, a pH value of the pH indicator solution is computed using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$.

However, the technique according to Non-Patent Document 1 does not particularly consider deterioration of the pH indicator solution. Therefore, ultraviolet rays may be incident into the pH indicator solution in the measurement cell to deteriorate the pH indicator, which reduces the measurement accuracy.

An object of the present invention is to provide an apparatus and a method for measuring the concentration of carbon dioxide in water that can correct a reduction in measurement accuracy based on deterioration of a pH indicator.

Another object of the present invention is to provide an apparatus and a method for measuring the concentration of carbon dioxide in water that generates an alarm signal if the measurement accuracy is reduced by a cause other than deterioration.

Still another object of the present invention is to provide an apparatus and a method for measuring the concentration of carbon dioxide in water that can reliably detect deterioration of a pH indicator.

Further another object of the present invention is to provide a carbon dioxide concentration measurement apparatus that can reduce the amount of a pH indicator used.

Yet another object of the present invention is to provide a carbon dioxide concentration measurement apparatus with a simple structure.

Means for Solving the Problems

An apparatus and a method for measuring a concentration of carbon dioxide in water according to the present invention use a measurement cell including a carbon dioxide permeable section that allows permeation of carbon dioxide but that does not allow permeation of water if the measurement cell is immersed in water. The measurement cell is filled with a pH indicator solution that changes in color in accordance with changes in pH and that has a carbon dioxide concentration that finally becomes equal to the concentration of carbon dioxide in water. The pH indicator solution is obtained by mixing a pH indicator and a solvent. The pH indicator solution establishes an equilibrium of:

$$HL^- \leftrightarrows H^+ + L^{2-}$$ [Chemical formula 2]

if the pH indicator solution is represented as $H_2L$.

The apparatus according to the present invention includes a spectrum measuring apparatus that measures an absorption spectrum of light absorbed by the pH indicator solution, an absorbance computing section, a pH value computing section, and a carbon dioxide concentration determining section.

The absorbance computing section computes from the absorption spectrum a first absorbance $A_1$ at a first peak absorption wavelength $\lambda_1$ which is equivalent to a concentration of $HL^-$ in the pH indicator solution, a second absorbance $A_2$ at a second peak absorption wavelength $\lambda_2$ which is equivalent to a concentration of $L^{2-}$ in the pH indicator solution, an isosbestic point absorbance $A_0$ at an isosbestic point wavelength at which the pH indicator solution does not show changes in absorbance in accordance with changes in pH, and a non-light-absorbing absorbance $A_b$ at a non-light-absorbing wavelength $\lambda_b$. The pH value computing section computes a pH value of the pH indicator solution using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$. The carbon dioxide concentration determining section determines the concentration of carbon dioxide in water from the computed pH value.

The apparatus according to the present invention further includes a deterioration determining section that computes a change rate $\Delta A_0$ of the isosbestic point absorbance $A_0$ and determines that the pH indicator solution is deteriorated when the change rate $\Delta A_0$ is reduced by a predetermined reduction rate or more. After the deterioration determining section determines deterioration of the pH indicator solution, the pH value computing section computes the pH value of the pH indicator solution using a corrected pH computation expression for correcting a deterioration of the pH value of the pH indicator solution on the basis of the change rate $\Delta A_0$ of the isosbestic point absorbance $A_0$.

According to the present invention, the absorbances $A_1$, $A_2$, and $A_b$ at the three wavelengths ($\lambda_1$, $\lambda_2$, and $\lambda_b$) are used to calculate the absorbance ratio $(A_1-A_b)/(A_2-A_b)$ of the difference $(A_1-A_b)$ between the first absorbance $A_1$ and the non-light-absorbing absorbance $A_b$ to the difference $(A_2-A_b)$ between the second absorbance $A_2$ and the non-light-absorbing absorbance $A_b$. Therefore, variations (a drift) in measurement values due to temperature or the like are offset, and it is not necessary to perform a correction for slight changes in concentration of the pH indicator. Theoretically, the apparatus performs an absolute measurement which requires no standard substance. According to the present invention, in addition, measurement can be performed also with a pH indicator whose basic spectrum and acid spectrum overlap each other at two peak wavelengths.

An example of the basic pH computation expression that can be used in the present invention is given below.

$$pH = pKa + \log\left(\frac{(A_2 - A_b)/(A_1 - A_b) - \varepsilon_{21}/\varepsilon_{11}}{\varepsilon_{22}/\varepsilon_{11} - (A_2 - A_b)/(A_1 - A_b)(\varepsilon_{12}/\varepsilon_{11})}\right) \quad \text{[Expression 1]}$$

In the above expression, the pH indicator solution establishes an equilibrium of:

$$HL^- \leftrightarrows H^+ + L^{2-}$$ [Chemical formula 3]

if the pH indicator solution is represented as $H_2L$.

In the above expression, pKa is a dissociation constant of the pH indicator solution. $\varepsilon_{11}$ and $\varepsilon_{12}$ are respective molar absorption coefficients of $HL^-$ and $L^{2-}$ at the first peak absorption wavelength $\lambda_1$. $\varepsilon_{21}$ and $\varepsilon_{22}$ are respective molar absorption coefficients of $HL^-$ and $L^{2-}$ at the second peak absorption wavelength $\lambda_2$.

As the corrected pH computation expression in contrast to the above basic pH computation expression, the following expression may be used.

$$pH = pKa + \log\left(\frac{(A_2 - (1-\Delta A_0)B_2 - A_b)/}{(A_1 - (1-\Delta A_0)B_1 - A_b) - \varepsilon_{21}/\varepsilon_{11}} \atop \frac{\varepsilon_{22}/\varepsilon_{11} - (A_2 - (1-\Delta A_0)B_2 - A_b)/}{(A_1 - (1-\Delta A_0)B_1 - A_b) \times (\varepsilon_{12}/\varepsilon_{11})}\right) \quad \text{[Expression 2]}$$

In the above expression, $\Delta A_0$ is the change rate of the isosbestic point absorbance. $B_1$ and $B_2$ are respective absorbances of an indicator decomposition substance at the first and second peak absorption wavelengths $\lambda_1$ and $\lambda_2$ (respective absorbances of a substance generated with all the indicator decomposed at the first and second peak absorption wavelengths $\lambda_1$ and $\lambda_2$. The absorbances $B_1$ and $B_2$ of the indicator decomposition substance can be measured in advance in the course of applying ultraviolet rays to the pH indicator solution for a long period to decompose the indicator.

The above expression allows pH measurement values to be corrected using the absorbances $B_1$ and $B_2$, measured in advance, of a new indicator decomposition substance, which is generated by deterioration and decomposition of the pH indicator, and the change rate $\Delta A_0$ of the isosbestic point absorbance even if the indicator decomposition substance absorbs light at two peak absorption wavelengths, namely the first and second peak absorption wavelengths $\lambda_1$ and $\lambda_2$. Thus, the measurement accuracy can be enhanced compared to the related art.

Preferably, the apparatus further includes a first alarm signal generating section that determines that an abnormality is occurring in the measurement cell, a light source, a light receiving element, or the like to generate an alarm signal if the con-light-absorbing absorbance $A_b$ is varied by a predetermined variation rate or more with reference to an initial value. The con-light-absorbing absorbance $A_b$ does not change basically. Thus, it is highly likely that an abnormality is occurring in the measurement cell, the light source, the light receiving element, or the like if the non-light-absorbing absorbance $A_b$ is changed. Practically, however, the non-light-absorbing absorbance $A_b$ can change under the influence of the temperature. Thus, erroneous generation of an alarm signal can be prevented by generating an alarm signal if the non-light-absorbing absorbance $A_b$ is varied by a predetermined variation rate or more with reference to an initial value. Examples of the abnormality in the measurement cell include entry of air bubbles into the measurement cell. Examples of the abnormality in the light source include a reduction in light intensity of the light source. Examples of the abnormality in the light receiving element include a significant reduction in sensitivity of the light receiving element.

The spectrum measuring apparatus may include a light source that emits measurement light to a light permeable section of the measurement cell, a light receiving element that receives the measurement light which has passed inside the light permeable section, and a measuring section that measures the absorption spectrum on the basis of an output of the light receiving element. In this case, the apparatus may further include a second alarm signal generating section that generates an alarm signal indicating that an abnormality is occurring in the light source or the light receiving element if an output of the light source or the output of the light receiving element is varied by a predetermined variation rate or more with reference to an initial value. That is, if the output of the light source or the output of the light receiving element is varied by a predetermined variation rate or more with reference to an initial value, the accuracy of the measurement results significantly reduces even if the functions of the other components are normal. Since the second alarm signal generating section is provided, an alarm signal indicating that an abnormality due to a specific cause is occurring can be generated to facilitate treatment of the occurred abnormality.

The deterioration determining section may determine that the pH indicator solution is deteriorated when an alarm signal is not input from either of the first alarm signal generating section and the second alarm signal generating section. This configuration can further enhance the measurement accuracy.

Preferably, the apparatus further includes a third alarm signal generating section that determines that an abnormality is occurring in the pH indicator solution in the measurement cell to generate an alarm signal if the non-light-absorbing absorbance $A_b$ is varied by a predetermined variation rate or more with reference to an initial value and an output of the light source or the output of the light receiving element is not varied by a predetermined variation rate or more with reference to an initial value. Since the third alarm signal generating section is provided, an alarm signal indicating that an abnormality specifically due to the pH indicator solution in the measurement cell is occurring can be generated to facilitate treatment of the generated abnormality.

Any desired process may be executed on the basis of the generated alarm signal. For example, if the third alarm signal generating section generates an alarm signal indicating an abnormality of the pH indicator solution, the pH indicator solution in the measurement cell may be changed. For this purpose, the apparatus may further include a change command generating section that generates a change command requesting a change of the pH indicator solution in the measurement cell, and an indicator solution changer that changes the pH indicator solution in the measurement cell when the change command is input. The change command generating section may output a change command not only when the change command is input but also when it is necessary to change the pH indicator solution.

The light source may be of any type. However, if the measurement apparatus operates on only a battery over a long period, it is preferable to reduce the power consumed by the light source as much as possible. Therefore, a light emitting diode with low power consumption is preferably used as the light source. However, the wavelength of a single light emitting diode is Limited. Therefore, the light source for measurement may be formed by combining a plurality of types of light emitting diodes with different wavelengths. The respective wavelengths of the plurality of types of light emitting diodes may be selected to allow measurement at the four wavelengths $\lambda_1, \lambda_2, \lambda_0$, and $\lambda_b$. In this way, it is possible to form a light source that supports required wavelengths using light emitting diodes with low power consumption.

If the indicator solution changer discussed above is used, the measurement cell and the indicator solution changer may be configured to form a pH indicator circulation path that allows circulation of the pH indicator solution through the carbon dioxide permeable section during measurement performed by the spectrum measuring apparatus, to discharge the pH indicator solution in the pH indicator circulation path from the pH indicator circulation path and to fill the pH indicator circulation path with a new pH indicator solution when the change command is input. Since the pH indicator circulation path is provided, the pH indicator solution can be repeatedly passed through in the carbon dioxide permeable section in the measurement cell. Thus, the length of the carbon dioxide permeable section can be reduced, and the amount of the pH indicator solution necessary for measurement can be reduced.

The measurement cell may include the carbon dioxide permeable section, a light permeable section that allows permeation of the light, and a circulation pump disposed in the pH indicator circulation path. The indicator solution changer may include a first switching valve disposed at a connection portion between a pH indicator solution supply path and the pH indicator circulation path and a second switching valve disposed at a connection portion between a pH indicator solution discharge path and the pH indicator circulation path. In this case, the indicator solution changer may be configured to operate the first and second switching valves to bring the pH indicator circulation path into a closed state by separating the pH indicator solution supply path and the pH indicator solution discharge path from the pH indicator circulation path during measurement, and to temporarily bring the pH indicator circulation path into an open state by connecting the pH indicator solution supply path and the pH indicator solution discharge path to the pH indicator circulation path and then bring the pH indicator circulation path back into the closed state when the change command is input. Herein, the term "closed state" refers to a state in which the pH indicator circulation path forms a closed circuit so that the indicator can circulate in the pH indicator circulation path. The term "open state" refers to a state in which the pH indicator circulation path is connected to the pH indicator solution supply path and the pH indicator solution discharge path so that the indicator in the pH indicator circulation path can be discharged from the pH indicator solution discharge path and the pH indicator circulation path can be filled with a new indicator from the pH indicator solution supply path. The indicator solution changer structured as described above can switch the pH indicator circulation path between the "closed state" and the "open state" with only the first and second switching valves. Thus, the indicator can be circulated and changed with a simple structure.

Preferably, at least the first and second switching valves and the circulation pump are mounted on a single insulating resin substrate, and the pH indicator solution supply path, the pH indicator solution discharge path, and at least a part of the pH indicator circulation path are formed in the insulating resin substrate by drilling. By adopting such a structure, not only the number of pipes necessary to form the pH indicator solution supply path, the pH indicator solution discharge path, and the pH indicator circulation path can be reduced, but also the structure of the measurement apparatus can be simplified.

In the method for measuring a concentration of carbon dioxide according to the present invention, an absorption spectrum of light absorbed by a pH indicator solution establishing an equilibrium of:

   [Chemical formula 4]

if the pH indicator solution is represented as $H_2L$ is measured.

Then, a first absorbance $A_1$ at a first peak absorption wavelength $\lambda_1$ which is equivalent to a concentration of $HL^-$ in the pH indicator solution, a second absorbance $A_2$ at a second peak absorption wavelength $\lambda_2$ which is equivalent to a concentration of $L^{2-}$ in the pH indicator solution, an isosbestic point absorbance $A_0$ at an isosbestic point wavelength at which the pH indicator solution does not show changes in absorbance in accordance with changes in pH, and a non-light-absorbing absorbance $A_b$ at a non-light-absorbing wavelength $\lambda_b$ are computed from the absorption spectrum. Then, a pH value of the pH indicator solution is computed using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$. The concentration of carbon dioxide in water is determined from the computed pH value. In this case, in the method for measuring a concentration of carbon dioxide in water according to the present invention, the change rate of the isosbestic point absorbance $A_0$ is measured, and it is determined that the pH indicator solution is deteriorated if the isosbestic point absorbance $A_0$ is reduced by a predetermined reduction rate or more with reference to an initial value. After deterioration of the pH indicator solution is determined, the pH value of the pH indicator solution is computed using a corrected pH computation expression for correcting a deterioration of the pH value of the pH indicator solution on the basis of the change rate $\Delta A_0$ of the isosbestic point absorbance $A_0$.

BRIEF DESCRIPTION OF DRAWINGS

FIG. 7 shows the configuration of an essential portion of an indicator solution change system for use to reduce the amount of the pH indicator solution used.

BEST MODE FOR CARRYING OUT THE INVENTION

Figure 1:
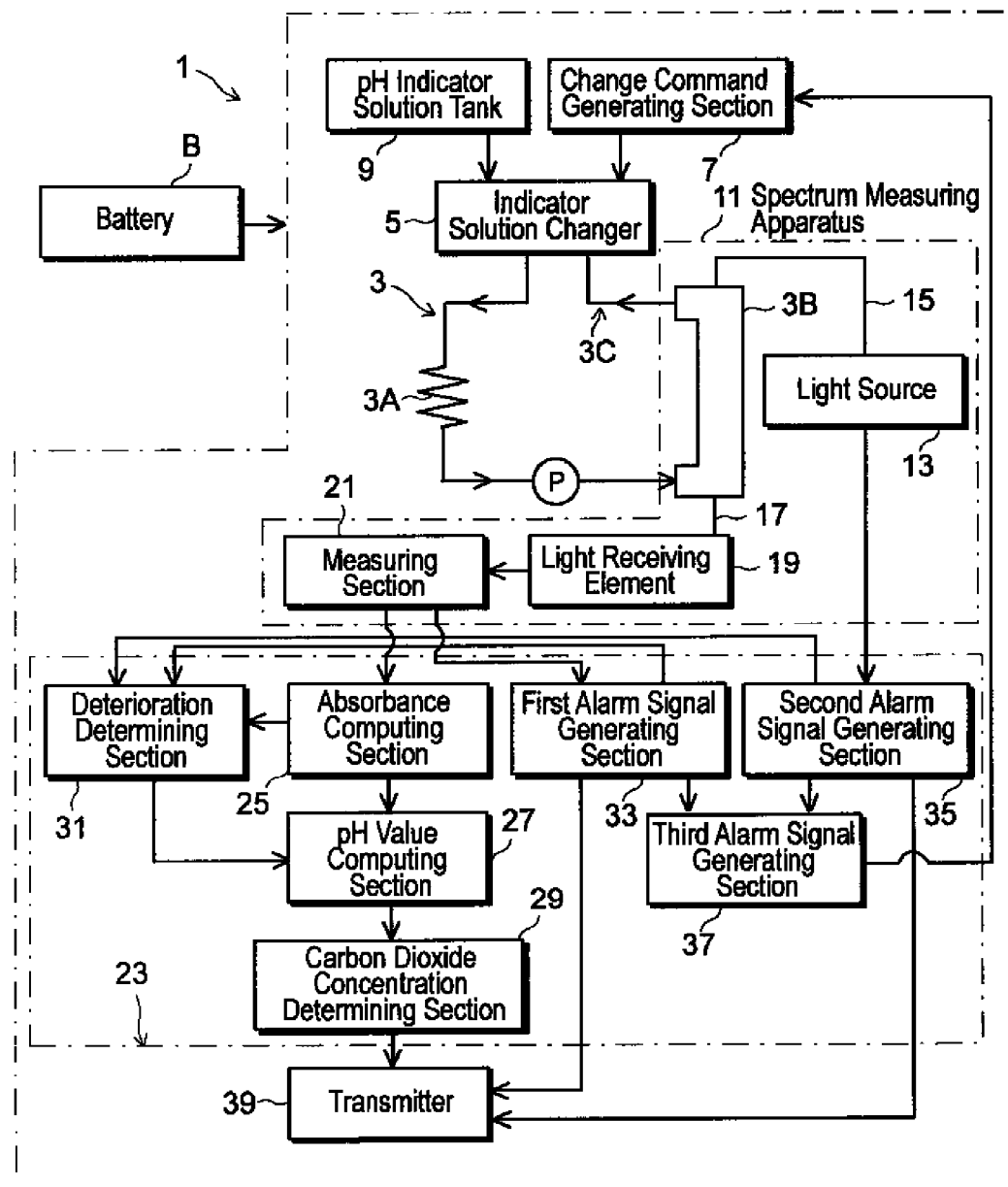
FIG. 1 is a block diagram showing the configuration of a carbon dioxide concentration measurement apparatus that implements a method according to an embodiment of the present invention.

An exemplary embodiment of an apparatus and a method for measuring the concentration of carbon dioxide in water according to the present invention will be described below with reference to the drawings. FIG. 1 is a block diagram showing an exemplary configuration of an embodiment of a carbon dioxide concentration measurement apparatus 1 that implements a method according to the present invention. The apparatus 1 operates on a battery B serving as a power source, and includes a measurement cell 3 including a carbon dioxide permeable section 3A that allows permeation of carbon dioxide but that does not allow permeation of water when the measurement cell 3 is immersed in water (which includes both seawater and freshwater). The measurement cell 3 further includes a light permeable section 3B that allows permeation of measurement light. As the carbon dioxide permeable section 3A, a material that functions as a gas exchange membrane, for example an AF Teflon tube (trademark), may be used. The carbon dioxide permeable section 3A and the light permeable section 3B are disposed in a pH indicator circulation path 3C. The measurement cell 3 is filled with a pH indicator solution that changes in color in accordance with changes in pH and that has a carbon dioxide concentration that finally becomes equal to the concentration of carbon dioxide in water. The pH indicator solution is obtained by mixing a pH indicator and a solvent. The pH indicator solution used in the present invention establishes an equilibrium of:

   [Chemical formula 5]

if the pH indicator solution is represented as $H_2L$, such as thymol blue and bromocresol purple.

A circulation pump P and an indicator solution changer 5 are disposed in the pH indicator circulation path 3C. The circulation pump P is driven by a pump control device (not shown), and operates at intervals of 6 hours, for example, to deliver the pH indicator solution containing carbon dioxide that has entered from water into the pH indicator solution through the carbon dioxide permeable section 3A to the light permeable section 3B. The indicator solution changer 5 replaces the pH indicator solution in the pH indicator circulation path 3C with an unused pH indicator solution in a pH indicator solution tank 9 when a change command to be discussed later is input from a change command generating section 7. The change command generating section 7 may be configured to regularly output a change command each time a predetermined number of measurements are performed.

Figure 2:
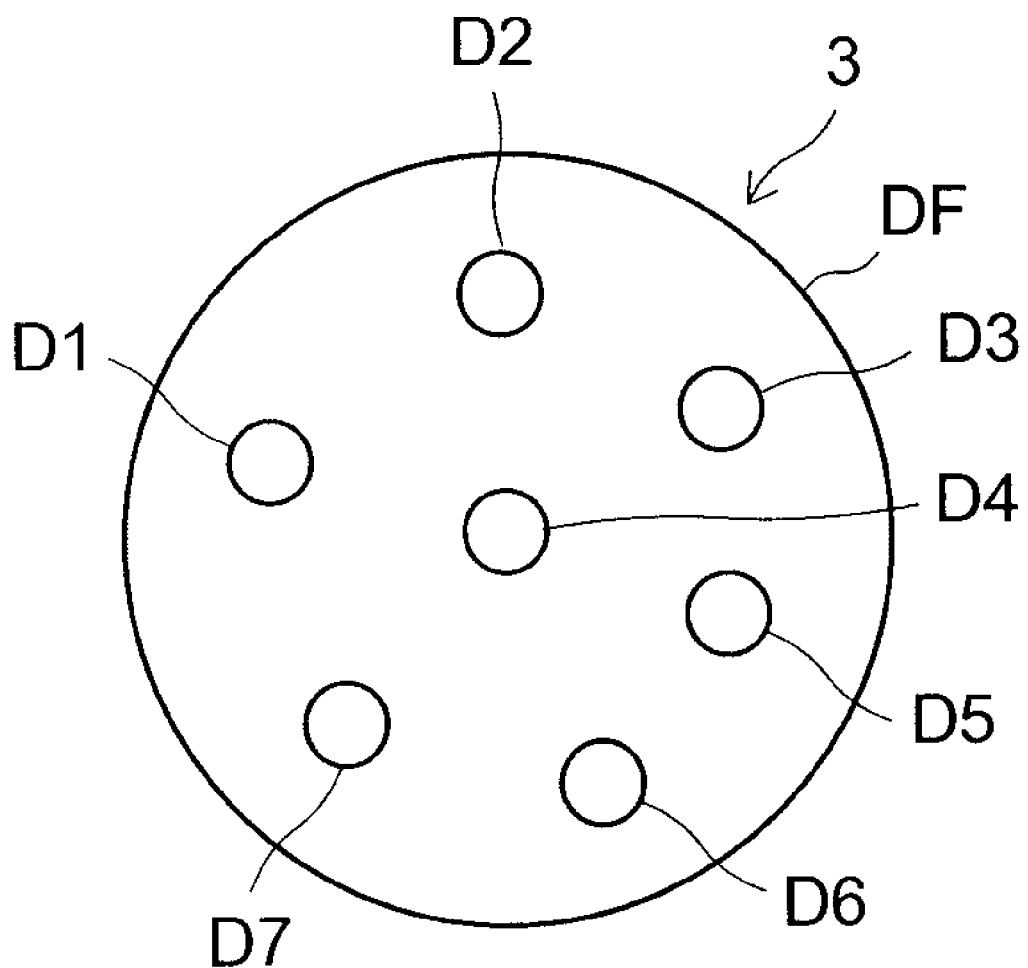
FIG. 2 shows an exemplary arrangement of light emitting diodes of a light source.

The carbon dioxide concentration measurement apparatus 1 also includes a spectrum measuring apparatus 11 that measures an absorption spectrum of light absorbed by the pH indicator solution. The spectrum measuring apparatus 11 includes a light source 13, first and second light passages 15 and 17 formed by an optical fiber, a light receiving element 19 that forms a spectrophotometer, and a measuring section 21. The light source 13 may be of any type. However, if the carbon dioxide concentration measurement apparatus 1 according to the embodiment operates on only the battery B over a long period, it is necessary to reduce the power consumed by the light source 13 as much as possible. In the embodiment, thus, a light emitting diode with low power consumption is used as the light source 13. However, the wavelength of a single light emitting diode is limited. Therefore, the light source 13 for measurement is formed by combining a plurality of types of light emitting diodes with different wavelengths. FIG. 2 shows an exemplary arrangement of the light emitting diodes of the light source. In the light source 13 shown in FIG. 2, seven light emitting diodes D1 to D7 are provided on a parabolic reflective plate DF. The shape of the reflective surface of the reflective plate DF is determined to converge the light emitted from the light emitting diodes D1 to D7. Of the seven light emitting diodes D1 to D7, three light emitting diodes D1 to D3 ace white light emitting diodes, two light emitting diodes D4 and D5 are red light emitting diodes, one light emitting diode D6 is a green light emitting diode, and one light emitting diode D7 is a blue light emitting diode. The light emitting diodes emit light at wavelengths corresponding to a range of 400 nm to 700 nm. The respective wavelengths of the light emitting diodes D1 to D7 are selected to allow measurement of four wavelengths $\lambda_1, \lambda_2, \lambda_0$, and $\lambda_b$ to be discussed later. A frosted glass plate (not shown) is placed in front of the reflective plate DF (in the light emission direction) so that light emitted from the light emitting diodes D1 to D7 is mixed by the frosted glass to be incident into the light passage 15 (FIG. 1) formed by an optical fiber. The light which has entered into the light passage 15 is incident into the light permeable section 3B of the measurement cell 3, passes through the inside of the pH indicator solution in the light permeable section 3B to be incident into the light passage 17 formed by an optical fiber, and is guided to the light receiving element 19 formed by a CCD or the like. A part of the light incident into the light permeable section 3B of the measurement cell 3 is absorbed by a substance in the pH indicator solution. As a result, the absorbance of the light absorbing substance can be computed by the measuring section 21 by analyzing the absorption spectrum of the light received by the light receiving element 19 which forms a spectrophotometer. For this purpose, the carbon dioxide concentration measurement apparatus 1 includes a measurement result processing section 23 that processes the measurement results of the spectrum measuring apparatus 11. The measurement result processing section 23 includes an absorbance computing section 25, a pH value computing section 27, a carbon dioxide concentration determining section 29, a deterioration determining section 31, and first to third alarm signal generating sections 33, 35, and 37.

Figure 3:
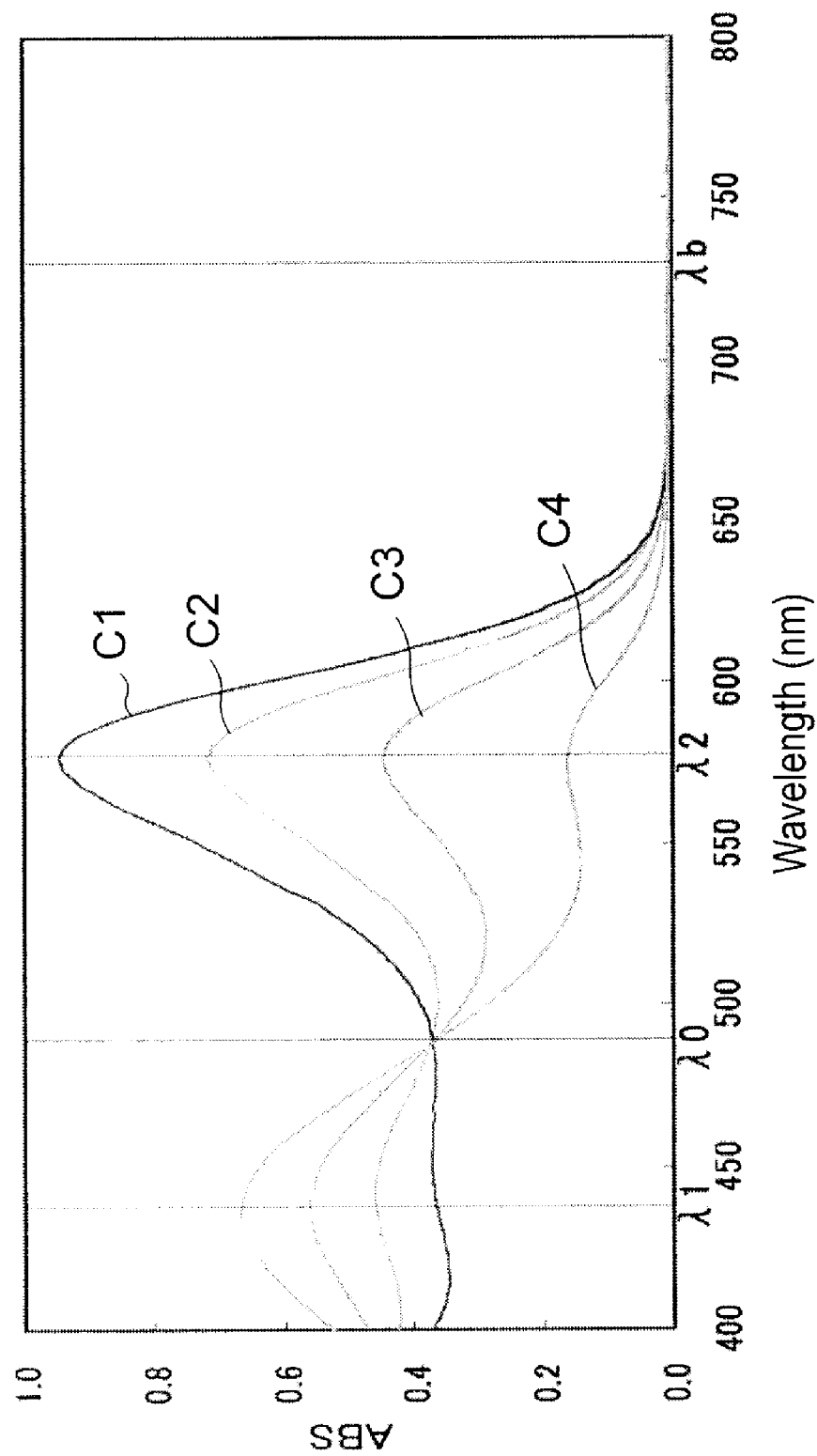
FIG. 3 shows an example of the absorption spectrum of a pH indicator.

The principles of the measurement of the concentration of carbon dioxide in water performed by the measurement result processing section 23 are described. FIG. 3 shows an example of the absorption spectrum of the pH indicator used in the following description. In FIG. 3, the horizontal axis represents the wavelength, and the vertical axis represents the absorbance. In FIG. 3, curves C1 to C4 indicate the respective absorption spectra of pH indicator solutions with different pHs. The carbon dioxide concentration is measured utilizing the fact that carbon dioxide becomes acidic when dissolved in water. Carbon dioxide that has passed through the carbon dioxide permeable section 3A of the measurement cell 3 and entered into the circulation path 3C is dissolved in the pH indicator solution to become acidic. Then, the color of the pH indicator solution in which the carbon dioxide is dissolved is measured to obtain the pH of the pH indicator solution, from which the carbon dioxide concentration of the pH indicator solution is determined. In order to determine the pH of the pH indicator solution, the absorbances (how much light at a specific wavelength is absorbed) at two peak absorption wavelengths, that is, first and second peak absorption wavelengths ($\lambda_1$ and $\lambda_2$ in FIG. 3), are measured from the color of the pH indicator, that is, the light absorption spectrum of the pH indicator. In general, a pH indicator has two peak absorption wavelengths of around 440 nm to 580 nm. The pH is calculated from the ratio of the absorbances at the two wavelengths using calculation expressions to be described in detail later. In the embodiment, an isosbestic point wavelength $\lambda_0$ at which the pH indicator solution does not show changes in absorbance in accordance with changes in pH and a non-light-absorbing wavelength $\lambda_b$ are utilized in addition to the first and second peak absorption wavelengths $\lambda_1$ and $\lambda_2$. Therefore, it is necessary that the light source 13 used in the embodiment should emit light at a wavelength longer than 670 nm at which no light is absorbed (with an absorbance of 0).

The absorbance is a value indicating how much light that as passed through a pH indicator is attenuated with reference to the intensity of light where light is not absorbed (where the pH indicator is not present). If the amount of light emitted from the light source around the first and second peak absorption wavelengths $\lambda_1$ and $\lambda_2$ is small, the amount of light around the first and second peak absorption wavelengths $\lambda_1$ and $\lambda_2$ is further reduced when the light is absorbed by the pH indicator to be attenuated, which relatively increases noise of a measurement instrument with respect to the output of the light to reduce the measurement accuracy. A difference $\Delta f$ in amount of light is provided in a wavelength width $\Delta x$ covered by each light receiving element portion in the light receiving element 19 which forms a spectrophotometer. Therefore, in a wavelength region in which the intensity of light changes drastically, slight changes in $\Delta x$ due to vibration or changes in temperature may easily cause changes in $\Delta f/\Delta x$ to reduce the measurement accuracy. Thus, the light source 13 uses a plurality of types of light emitting diodes as discussed above to serve as a light source that emits light including necessary wavelengths and that ensures a necessary and sufficient amount of light around the first and the second peak absorption wavelengths.

Returning to FIG. 1, the absorbance computing section 25 computes, from the absorption spectrum measured by the measuring section 21 of the spectrum measuring apparatus 11, a first absorbance $A_1$ at the first peak absorption wavelength $\lambda_1$ which is equivalent to a concentration of $HL^-$ in the pH indicator solution, a second absorbance $A_2$ at the second peak absorption wavelength $\lambda_2$ which is equivalent to a concentration of $L^{2-}$ in the pH indicator solution, an isosbestic point absorbance $A_0$ at an isosbestic point wavelength $\lambda_0$ at which the pH indicator solution does not show changes in absorbance in accordance with changes in pH, and a non-light-absorbing absorbance $A_b$ at a non-light-absorbing wavelength $\lambda_b$. The pH value computing section 27 then computes a pH value of the pH indicator solution using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$.

An example of the basic pH computation expression is given below.

$$\text{pH} = pKa + \log\left(\frac{(A_2-A_b)/(A_1-A_b) - \varepsilon_{21}/\varepsilon_{11}}{\varepsilon_{22}/\varepsilon_{11} - (A_2-A_b)/(A_1-A_b)(\varepsilon_{12}/\varepsilon_{11})}\right) \quad \text{[Expression 3]}$$

The above expression is based on the assumption that the pH indicator solution establishes an equilibrium of:

$$HL^- \rightleftharpoons H^+ + L^{2-} \quad \text{[Chemical formula 6]}$$

if the pH indicator solution is represented as $H_2L$.

In the formula, H is a proton and L is a basic ion. In this case, pKa is a dissociation constant of the pH indicator solution. $\varepsilon_{11}$ and $\delta_{12}$ are respective molar absorption coefficients of $HL^-$ and $L^{2-}$ at the first peak absorption wavelength $\lambda_1$. $\varepsilon_{21}$ and $\varepsilon_{22}$ are respective molar absorption coefficients of $HL^-$ and $L^{2-}$ at the second peak absorption wavelength $\lambda_2$. The pH value computing section 27 stores in advance the constant pKa and the coefficients $\varepsilon_{11}$, $\varepsilon_{12}$, $\varepsilon_{21}$, and $\varepsilon_{22}$ in accordance with the pH indicator used. The computation using the above expression is executed using a microcomputer. Then, the carbon dioxide concentration determining section 29 determines the concentration of carbon dioxide in water from the computed pH value by referencing a data table prepared by measuring in advance the relationship between the pH indicator solution used and the concentration of carbon dioxide dissolved. The carbon dioxide concentration determined by the carbon dioxide concentration determining section 29 is stored in an internal memory. Data on the carbon dioxide concentration stored in the memory are then regularly transmitted from a transmission device 39 to a monitoring center.

In the embodiment, further, the deterioration determining section 31 measures a change rate $\Delta A_0$ of the isosbestic point absorbance $A_0$. The deterioration determining section 31 determines that the pH indicator solution is deteriorated when the isosbestic point absorbance $A_0$ is reduced by a predetermined change rate or more with reference to an initial value. The isosbestic point absorbance $A_0$ changes in accordance with changes in concentration of the pH indicator, and thus the deterioration state of the pH indicator can be determined by observing the change rate $\Delta A_0$. As the initial value discussed above, an initial value of the isosbestic point absorbance $A_0$ at the start of the measurement is stored in the memory. Then, the change rate $\Delta A_0$ of the isosbestic point absorbance $A_0$ with respect to the initial value is computed in the course of repeatedly performing a measurement periodically at intervals of a predetermined time (for example, at intervals of 6 hours). In a specific example, it may be determined that the pH indicator solution is deteriorated if the change rate $\Delta A_0$ of the isosbestic point absorbance $A_0$ is reduced by 1% or more with respect to the initial value. The reference may be different depending on the pH indicator used, and may also be different depending on the temperature of the use environment. In the embodiment, in order to further enhance the determination accuracy, the deterioration determining section 31 determines that the pH indicator solution deteriorated only if an alarm signal is not input from either of the first alarm signal generating section 33 or the second alarm signal generating section 35 to be discussed later.

After the deterioration determining section 31 determines deterioration of the pH indicator solution, the pH value computing section 27 computes the pH value of the pH indicator solution using a corrected pH computation expression for correcting a deterioration of the pH value of the pH indicator solution on the basis of the change rate $\Delta A_0$ of the isosbestic point absorbance $A_0$. The corrected pH computation expression is given below.

$$\text{pH} = pKa + \log\left(\frac{(A_2 - (1-\Delta A_0)B_2 - A_b)/}{(A_1 - (1-\Delta A_0)B_1 - A_b) - \varepsilon_{21}/\varepsilon_{11}}{\varepsilon_{22}/\varepsilon_{11} - (A_2 - (1-\Delta A_0)B_2 - A_b)/}{(A_1 - (1-\Delta A_0)B_1 - A_b)\times(\varepsilon_{12}/\varepsilon_{11})}\right) \quad \text{[Expression 4]}$$

Figure 4:
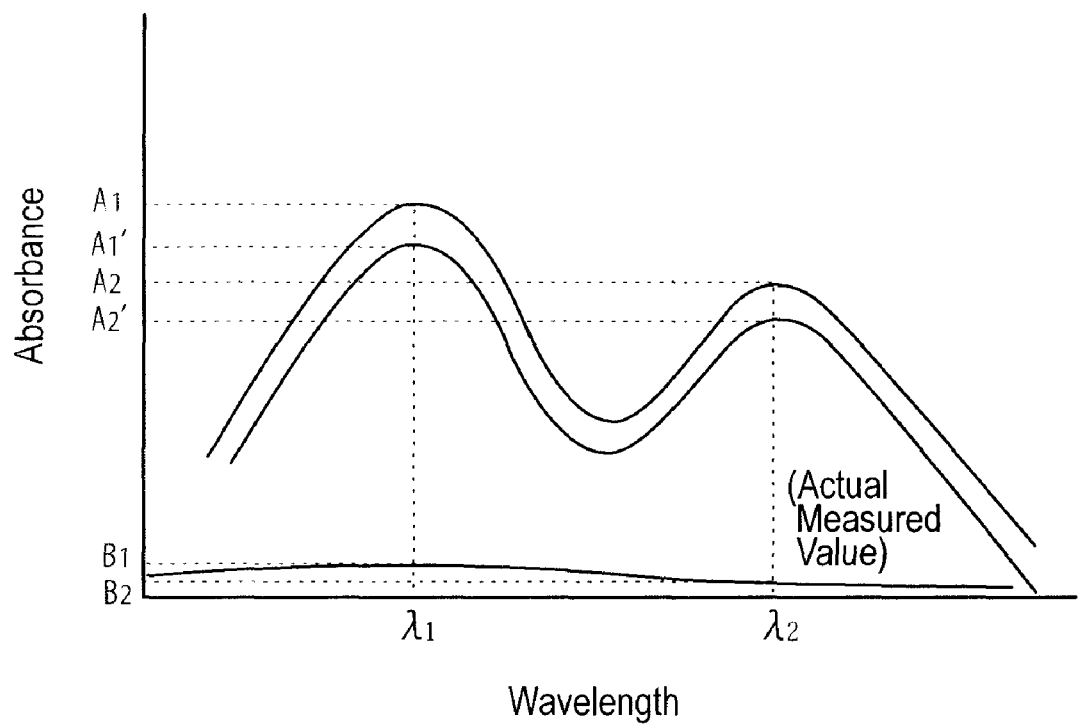
FIG. 4 shows an example of the relationship between the absorbances of an indicator decomposition substance and other absorbances.

In the above expression, $B_1$ and $B_2$ are respective absorbances of an indicator decomposition substance at the first and second peak absorption wavelengths $\lambda_1$ and $\lambda_2$ (with all the indicator decomposed). $B_1$ and $B_2$ are measured in advance in the course of applying ultraviolet rays to the indicator for a long period to decompose the indicator. If the first absorbance $A_1$ and the second absorbance $A_2$ are changed to $A_1'$ and $A_2'$ along with deterioration of the indicator, the relationship of $A_1'=A_1-B_1$ and $A_2'=A_2-B_2$ is established. The relationship is shown in FIG. 4. In the above expression, $(1-\Delta A_0)B_2$ and $(1-\Delta A_0)B_1$ are equivalent to changes due to the decomposition into the indicator decomposition substance. The use of the above expression allows pH measurement values to be corrected using the change rate $\Delta A_0$ of the isosbestic point absorbance even if a new substance generated by deterioration and decomposition of the pH indicator absorbs light at two peak absorption wavelengths, namely the first and second peak absorption wavelengths $\lambda_1$ and $\lambda_2$. Thus, the measurement accuracy can be enhanced compared to the related art.

Table 1 below shows the results of calculation performed to verify the effectiveness of the correction which uses the above expression. The calculation results below were obtained with $B_1$ and $B_2$ in the corrected pH computation expression respectively set to 0.03 and 0.01 and using the pKa and $\varepsilon$ values of the pH indicator (thymol blue).

TABLE 1

| $\Delta A_0$ | $A_1$ | $A_2$ | $A_2/A_1$ | pH | Corrected $A_1$ | Corrected $A_2$ | Corrected $A_2/A_1$ | Corrected PH | Difference |
|---|---|---|---|---|---|---|---|---|---|
| 1.0 | 0.400 | 0.600 | 1.500 | 8.376 | 0.400 | 0.600 | 1.50 | 8.376 | 0.000 |
| 0.9 | 0.363 | 0.541 | 1.490 | 8.373 | 0.360 | 0.540 | 1.50 | 8.376 | −0.003 |
| 0.8 | 0.326 | 0.482 | 1.479 | 8.369 | 0.320 | 0.480 | 1.50 | 8.376 | −0.007 |
| 0.7 | 0.289 | 0.423 | 1.464 | 8.364 | 0.280 | 0.420 | 1.50 | 8.376 | −0.012 |
| 0.6 | 0.252 | 0.364 | 1.444 | 8.358 | 0.240 | 0.360 | 1.50 | 8.376 | −0.018 |
| 0.5 | 0.215 | 0.305 | 1.419 | 8.349 | 0.200 | 0.300 | 1.50 | 8.376 | −0.027 |

The above example is based on the assumption that the concentration of carbon dioxide in the pH indicator solution is constant (i.e. the pH is constant). Since the indicator decomposition substance absorbs light at the first and second peak absorption wavelengths $\lambda_1$ and $\lambda_2$, the absorbances $A_1$ and $A_2$ before a correction (actual measurement values) are actual measurement values obtained by adding the absorbance of the indicator decomposition substance to the absorbance of the pH indicator. Therefore, as the decomposition of the indicator progresses (as the value of $\Delta A_0$ becomes smaller) the value of $A_2/A_1$ becomes smaller than that before the decomposition. In the corrected expression, changes due to the absorbances $B_1$ and $B_2$ of the indicator decomposition substance are subtracted, and thus both $A_1$ and $A_2$ reduce at the same proportion even if the indicator is decomposed. Therefore, the pH value does not change even when 50% of the indicator is decomposed (the value of $\Delta A_0$ becomes 0.5). The rightmost column of the above table titled "Difference" indicates how much the actual measurement values (uncorrected values) and the corrected values are different from each other. The carbon dioxide concentration measurement apparatus used in the test has a resolution of 0.001 pH, and thus can detect the difference with only 10% of the indicator decomposed (when the value of $\Delta A_0$ becomes 0.1). For example, the pH difference with 30% of the indicator decomposed is 0.012, which is converted into a difference of 10 u atm or more of carbon dioxide, which is five times or more the measurement accuracy of the apparatus. Thus, it is found that the correction which uses the above expression is effective in maintaining the measurement accuracy of the apparatus. The computation expression and the correction expression described above also enables measurement with a pH indicator whose basic $L^{2-}$ spectrum and $HL^-$ spectrum overlap each other (are the same as each other) at the two peak wavelengths.

Table 2 below shows the results of calculation performed to verify the effectiveness of the correction which uses the above expression also for a pH indicator whose basic $L^{2-}$ spectrum and $HL^-$ spectrum overlap each other (are the same as each other) at the two peak wavelengths. The calculation results in Table 2 below were obtained with $B_1$ and $B_2$ in the corrected pH computation expression respectively set to 0.08 and 0.05 and using pKa and $\epsilon$ values of the pH indicator (bromocresol purple).

In the corrected expression, the decomposition due to the absorbances $B_1$ and $B_2$ of the indicator decomposition substance is subtracted, and thus both $A_1$ and $A_2$ reduce at the same proportion even if the indicator is decomposed. Therefore, the pH value does not change even if 50% of the indicator is decomposed (the value of $\Delta A_0$ becomes 0.5). The rightmost column of Table 2 above titled "Difference" indicates how much the actual measurement values (uncorrected values) and the corrected values are different from each other.

In the embodiment, as shown in FIG. 1, the apparatus further includes the first alarm signal generating section 33 that determines that an abnormality is occurring in the measurement cell 3, the light source 13, the light receiving element 19, or the like to generate an alarm signal if the non-light-absorbing absorbance $A_b$ is varied by a predetermined variation rate or more with reference to an initial value. The non-light-absorbing absorbance $A_b$ does not change in the first place. Thus, it is highly that an abnormality is occurring in the measurement cell 3, the light source 13, the light receiving element 19, or the like if the non-light-absorbing absorbance $A_b$ is changed. Practically, however, the non-light-absorbing absorbance $A_b$ can change under the influence of the temperature. Thus, erroneous generation of an alarm signal can be prevented by generating an alarm signal if the non-light-absorbing absorbance $A_b$ is reduced by a predetermined variation rate or more (specifically, 1% or more, for example) with reference to an initial value. Examples of the abnormality in the measurement cell 3 include entry of air bubbles into the light permeable section 3B in the measurement cell 3 and intrusion of water. Examples of the abnormality in the light source 13 include a voltage drop due to a failure of a power source for the light source 13 and a reduction in light intensity (light amount) due to a breakage. Examples of the abnormality in the light receiving element 19 include a significant reduction in sensitivity of the light receiving element.

In the embodiment, moreover, the apparatus further includes the second alarm signal generating section 35 that generates an alarm signal indicating that an abnormality is occurring in the light source 13 or the light receiving element 19 if an output of the light source 13 or an output of the light receiving element 19 is varied (reduced) by a predetermined variation rate (several percent, for example 1 to 3%) or more with reference to an initial value (a value measured during an

TABLE 2

| $\Delta A_0$ | $A_1$ | $A_2$ | $A_2/A_1$ | pH | Corrected $A_1$ | Corrected $A_2$ | Corrected $A_2/A_1$ | Corrected PH | Difference |
|---|---|---|---|---|---|---|---|---|---|
| 1.0 | 0.500 | 0.500 | 1.000 | 7.759 | 0.500 | 0.500 | 1.000 | 7.759 | 0.000 |
| 0.9 | 0.458 | 0.455 | 0.993 | 7.756 | 0.450 | 0.450 | 1.000 | 7.759 | −0.003 |
| 0.8 | 0.416 | 0.410 | 0.986 | 7.752 | 0.400 | 0.400 | 1.000 | 7.759 | −0.007 |
| 0.7 | 0.374 | 0.365 | 0.976 | 7.747 | 0.350 | 0.350 | 1.000 | 7.759 | −0.011 |
| 0.6 | 0.332 | 0.320 | 0.964 | 7.741 | 0.300 | 0.300 | 1.000 | 7.759 | −0.017 |
| 0.5 | 0.290 | 0.275 | 0.948 | 7.734 | 0.250 | 0.250 | 1.000 | 7.759 | −0.025 |

Similarly to the example of Table 1, the above example in Table 2 is also based on the assumption that the concentration of carbon dioxide in the pH indicator solution is constant (i.e. the pH is constant). Since the indicator decomposition substance absorbs light at the first and second peak absorption wavelengths $\lambda_1$ and $\lambda_2$, the absorbances $A_1$ and $A_2$ before a correction (actual measurement values) are actual measurement values obtained by adding the absorbance of the indicator decomposition substance to the absorbance of the pH indicator. Therefore, as the decomposition of the indicator progresses (as the value of $\Delta A_0$ becomes smaller), the value of $A_2/A_1$ becomes smaller than that before the decomposition.

inspection of the measurement apparatus before the start of use). That is, if the output of the light source 13 or the output of the light receiving element 19 is varied by a predetermined variation rate or more with reference to an initial value, the accuracy of the measurement results significantly reduces even if the functions of the other components are normal. Providing the thus configured second alarm signal generating section 35 allows generation of an alarm signal indicating that an abnormality due to a specific cause is occurring to facilitate treatment of the generated abnormality.

The apparatus further includes the third alarm signal generating section 37 that determines that an abnormality is occurring in the pH indicator solution in the measurement cell to generate an alarm signal if the non-light-absorbing absorbance $A_b$ is varied by a predetermined variation rate (for example, 1%) or more with reference to an initial value and the output of the light source 13 or the output of the light receiving element 19 is not reduced by a predetermined variation rate (several percent, for example 1 to 3%) or more with reference to an initial value. Providing the thus configured third alarm signal generating section 37 allows generation of an alarm signal indicating that an abnormality specifically due to the pH indicator solution in the measurement cell 3 is occurring to facilitate treatment of the generated abnormality.

Any desired process may be executed on the basis of the generated alarm signal. For example, if the third alarm signal generating section 37 generates an alarm signal indicating an abnormality of the pH indicator solution, the pH indicator solution in the measurement cell 3 may be changed. For this purpose, the alarm signal generated by the third alarm signal generating section 37 is input to the change command generating section 7. In response to the alarm signal, the change command generating section 7 outputs a change command requesting a change of the pH indicator solution in the measurement cell 3 to the indicator solution changer 5. When the change command is input, the indicator solution changer 5 operates to change the pH indicator solution in the measurement cell 3. The first to third alarm signal generating sections 33, 35, and 37 are reset when the change operation is started or ended. The deterioration determining section 31 is also reset to return the pH value computing section 27 back to the use of the basic pH computation expression.

If one of the first and second alarm signal generating sections 33 and 35 generates an alarm signal alone, the alarm signal is sent to the transmitter 39. When the alarm signal is received, the transmitter 39 transmits information including the content of the alarm signal to a distant monitoring center. The monitoring center reads the content of the alarm signal to determine to discontinue the use of the received data or make arrangements for a repair.

Figure 5:
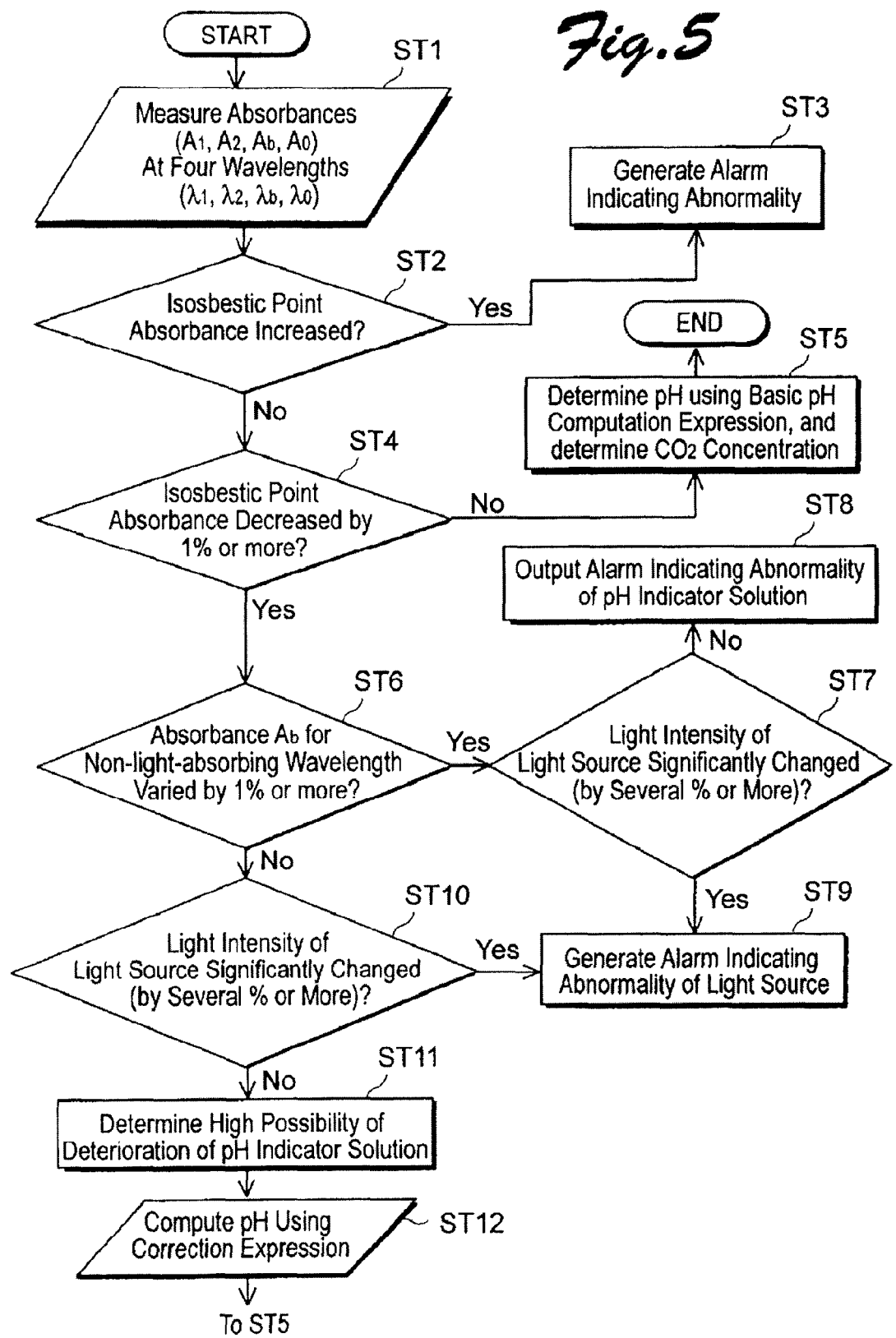
FIG. 5 is a flowchart showing an algorithm of a program used in a computer to implement the method according to the present invention using the measurement apparatus of FIG. 1, showing a portion of the algorithm related to determination of deterioration and generation of an alarm signal during one measurement.

FIG. 5 is a flowchart showing an algorithm of a program used in a computer to implement the method according to the present invention using the measurement apparatus of FIG. 1, showing a portion of the algorithm related to determination of deterioration and generation of an alarm signal during one measurement. In step ST1, an absorption spectrum of light absorbed by the pH indicator solution is measured. Then, a first absorbance $A_1$ at a first peak absorption wavelength $\lambda_1$ which is equivalent to a concentration of HL in the pH indicator solution, a second absorbance $A_2$ at a second peak absorption wavelength $\lambda_2$ which is equivalent to a concentration of $L^{2-}$ in the pH indicator solution, an isosbestic point absorbance $A_0$ at an isosbestic point wavelength at which the pH indicator solution does not show changes in absorbance in accordance with changes in pH, and a non-light-absorbing absorbance $A_b$ at a non-light-absorbing wavelength $\lambda_b$ are computed from the absorption spectrum. Then, a pH value of the pH indicator solution is computed using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$.

In step ST2, it is determined whether or not the isosbestic point absorbance $A_0$ is increased. The isosbestic point absorbance $A_0$ is not increased unless an abnormality occurs in the light source or air bubbles intrude or the like. Thus, if the determination result in ST2 is Yes, the process proceeds to step ST3 so generate an alarm signal indicating an abnormality. If the isosbestic point absorbance $A_0$ is not increased, the process proceeds to step ST4. In step ST4, the variation rate of the isosbestic point absorbance $A_0$ with respect to an initial value is computed. In a specific example, if the isosbestic point absorbance $A_0$ is not reduced by 1% or more with respect to the initial value, the process proceeds to step ST5, where pH is determined using the basic pH computation expression, and thereafter the carbon dioxide concentration is computed on the basis of the determined pH. The computation results are stored in a memory to terminate the process. If it is determined in step ST4 that the isosbestic point absorbance $A_0$ is reduced by 1% or more with respect to the initial value, the process proceeds to step ST6, where it is determined whether or not the non-light-absorbing absorbance $A_b$ is varied by a predetermined variation rate (1%) or more with reference to an initial value. If the non-light-absorbing absorbance $A_b$ is varied by the predetermined variation rate or more with reference to the initial value, the process proceeds to step ST7, where it is determined whether or not the amount of light emitted from the light source 13 is significantly changed (by several percent or more). Significant changes in output of the light source 13 may be determined on the basis of changes in output of the light receiving element 19. If the amount of light emitted from the light source 13 and received by the light receiving element is not significantly changed (by several percent or more) in step ST7, it is determined in step ST8 that an abnormality such as entry of air bubbles into the pH indicator solution or deterioration of the pH indicator solution which makes it inappropriate for use is occurring. If such a determination is made, an alarm signal is output to the change command generating section 7. As a result, the pH indicator solution in the measurement cell 3 is changed. If an abnormality in the light source 13 (or an abnormality in the light receiving element) is determined in step ST7, the process proceeds to step ST9 to generate an alarm signal reporting an abnormality in the light source.

If it is determined in step ST6 that the non-light-absorbing absorbance $A_b$ is not varied (reduced) by a predetermined variation rate (1%) or more with reference to the initial value, the process proceeds to step ST10. In step ST10, as in step ST7, it is determined whether or not the amount of light emitted from the light source 13 is significantly changed (by several percent or more). The process proceeds to step ST9 if the determination result is Yes, and to step ST11 if the determination result is No. In step ST11, it is determined that the pH indicator solution is deteriorated to such a degree that the pH computation requires a correction. Then, the process proceeds to step ST12, after which the pH computation is executed using the corrected pH computation expression. Then, the process proceeds from step ST12 to step ST5, where the carbon dioxide concentration is determined utilizing the concentration determination step in step ST5. Subsequently, the measurement is executed at intervals of a predetermined time.

In the embodiment shown in FIG. 1 and the flowchart shown in FIG. 5, it is determined whether or not the isosbestic point absorbance $A_0$ is changed by a cause other than deterioration of the pH indicator solution before the deterioration of the pH indicator solutions finally determined. Thus, the measurement accuracy is considerably high. In principle, however, it may be determined that the pH indicator solution is deteriorated when the change rate $\Delta A_0$ of the isosbestic point absorbance $A_0$ is reduced by a predetermined reduction rate or more. In this case, the first to third alarm signal generating sections 33, 35, and 37 are not necessary. The change command generating section 7 may be configured to regularly generate a change command.

It is a matter of course that the present invention is also applicable to a case where computation expressions other than the two types of computation expressions used in the embodiment are used.

Figure 6:
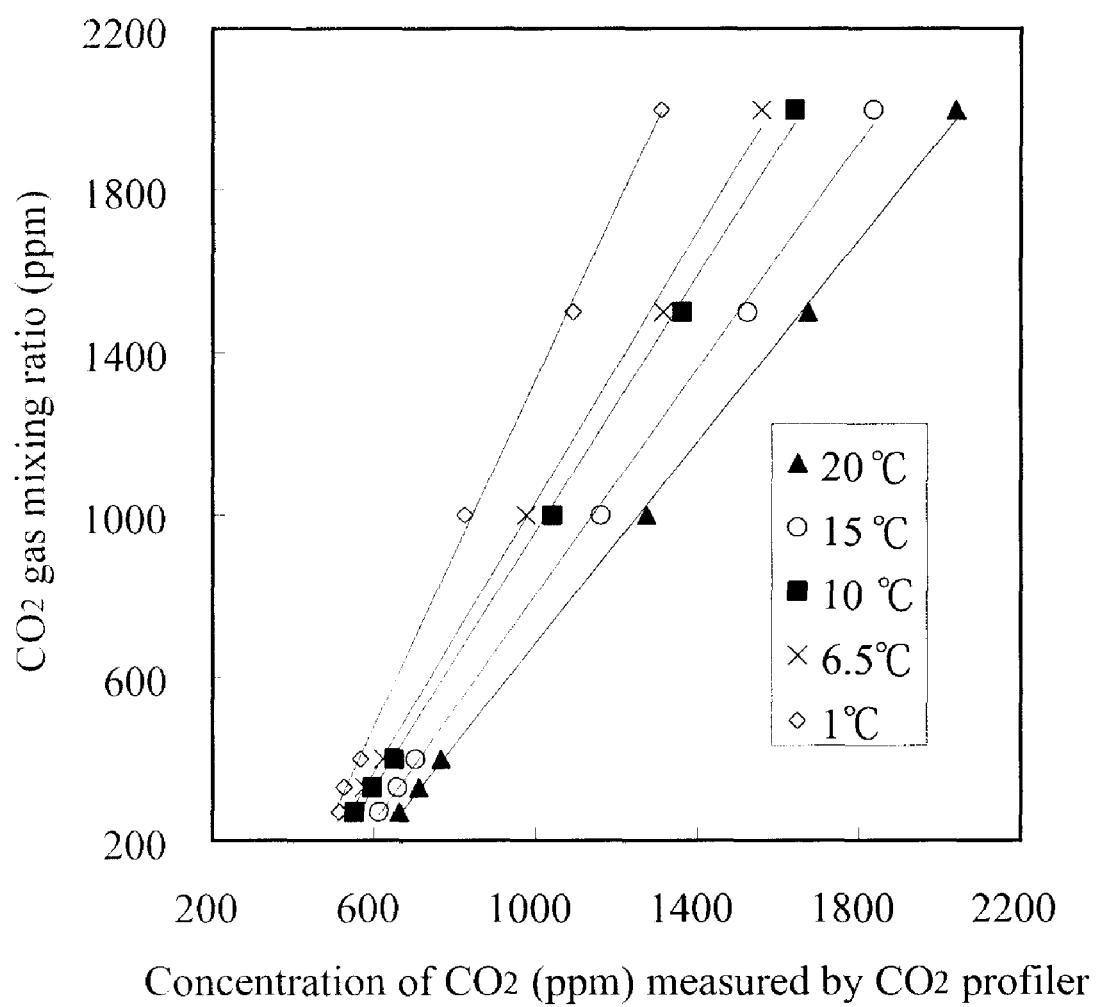
FIG. 6 shows the results of measuring changes in carbon dioxide concentration at different temperatures.

According to the embodiment, stable measurement can be performed at various temperatures. This is indicated by measurement data shown in FIG. 6. FIG. 6 shows the changes of results of measuring in carbon dioxide concentration at different temperatures. Changes in measurement results remain linear even at different temperatures. Thus, it is found when viewed relatively that stable measurement can be performed at various temperatures.

FIG. 7 shows the configuration of an essential portion of an indicator solution change system for use to reduce the amount of the pH indicator solution used. In the system, a measurement cell 103 and an indicator solution changer 105 are configured to form a pH indicator circulation path 103C, in which a pH indicator solution is circulated through a carbon dioxide permeable section 103A, a light permeable section 103B, and a circulation pump P, during measurement performed by the spectrum measuring apparatus discussed above. The indicator solution changer 105 includes a first switching valve V1 disposed at a connection portion between a pH indicator solution supply path FP0 and the pH indicator circulation path 103C and a second switching valve V2 disposed at a connection portion between a pH indicator solution discharge path FP6 and the pH indicator circulation path 103C. The first and second switching valves V1 and V2 are each formed by a three-way valve. The pH indicator circulation path 103C includes a flow path FP1 located between the first switching valve V1 and the second switching valve V2, a flow path FP2 located between the first switching valve V1 and the circulation pump P, a flow path FP3 located between the circulation pump P and the carbon dioxide permeable section 103A, a flow path FP4 located between the carbon dioxide permeable section 103A and the light permeable section 103B, and a flow path FP5 located between the light permeable section 103B and the second switching valve V2. In the example, the carbon dioxide permeable section 103A is formed by an AF Teflon tube (trademark).

During measurement, the indicator solution changer 105 switches the first and second switching valves V1 and V2 into a first state in which the pH indicator solution supply path FP0 and the pH indicator solution discharge path FP6 are separated from the pH indicator circulation path 103C to bring the pH indicator circulation path 103C into a closed state. When a change command is input, the indicator solution changer 105 switches the first and second switching valves V1 and V2 into a second state in which the pH indicator solution supply path FP0 and the pH indicator solution discharge path FP6 are connected to the pH indicator circulation path 103C to temporarily bring the pH indicator circulation path 103C into an open state, and thereafter returns the first and second switching valves V1 and V2 into the first state to bring the pH indicator circulation path 103C into the closed state again.

The indicator solution changer 105 can switch the pH indicator circulation path between the "closed state" and the "open state" with only the first and second switching valves V1 and V2. Thus, the indicator can be circulated and changed with a simple structure. The pH indicator solution in the pH indicator circulation path 103C can be discharged from the pH indicator circulation path to fill the pH indicator circulation path with a new pH indicator solution when a change command is input. Since the pH indicator circulation path 103C is provided, the pH indicator solution can be repeatedly passed through in the carbon dioxide permeable section 103A in the measurement cell 103. Thus, the length of the carbon dioxide permeable section 103A can be reduced, and the amount of the pH indicator solution necessary for measurement can be reduced.

Figure 8A:
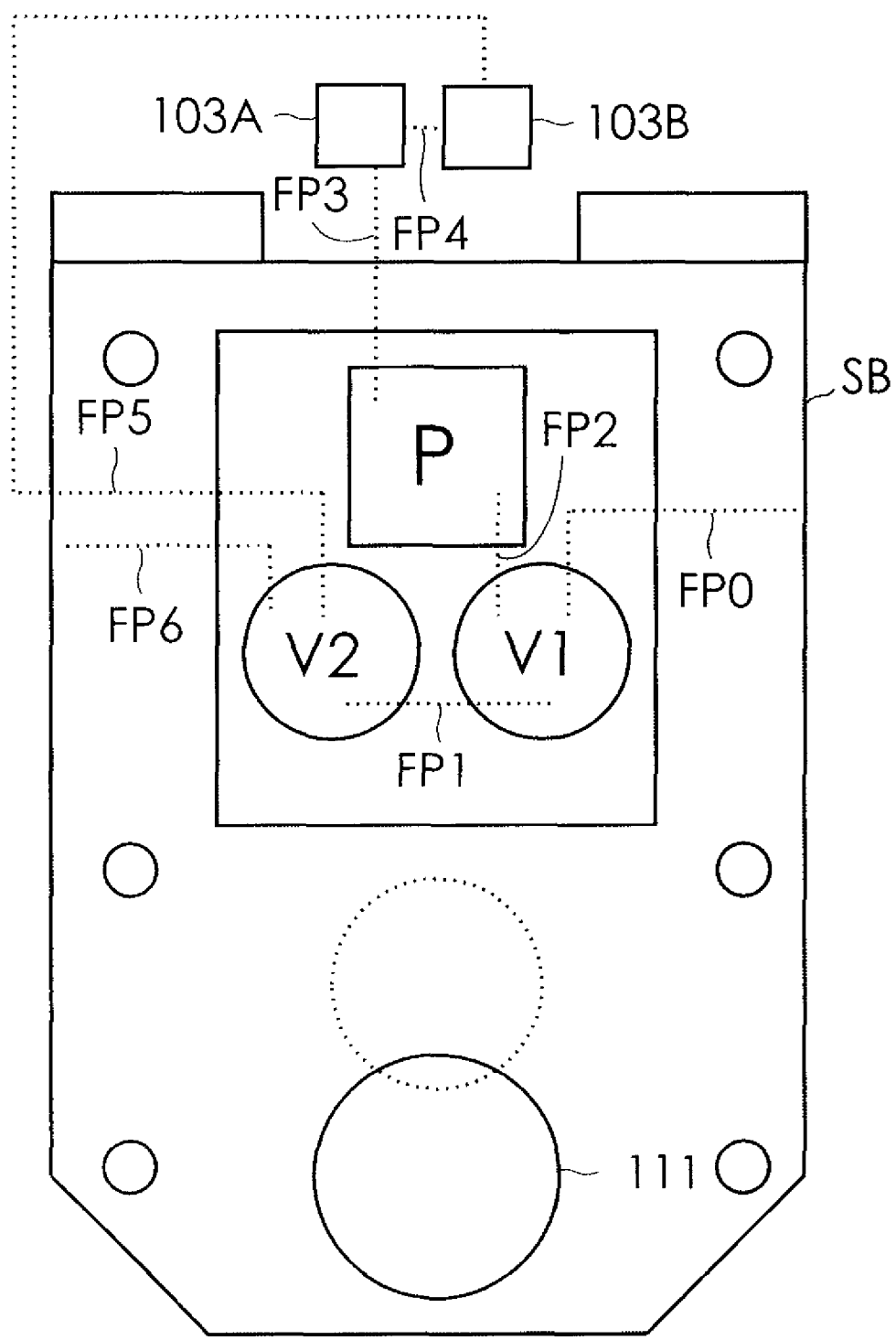
FIGS. 8A and 8B are a plan view and a right side view, respectively, of an example of a unit (an acrylic manifold) obtained by mounting first and second switching valves, a circulation pump, and a main portion of a spectrum measuring apparatus on a single insulating resin substrate.
Figure 8B:
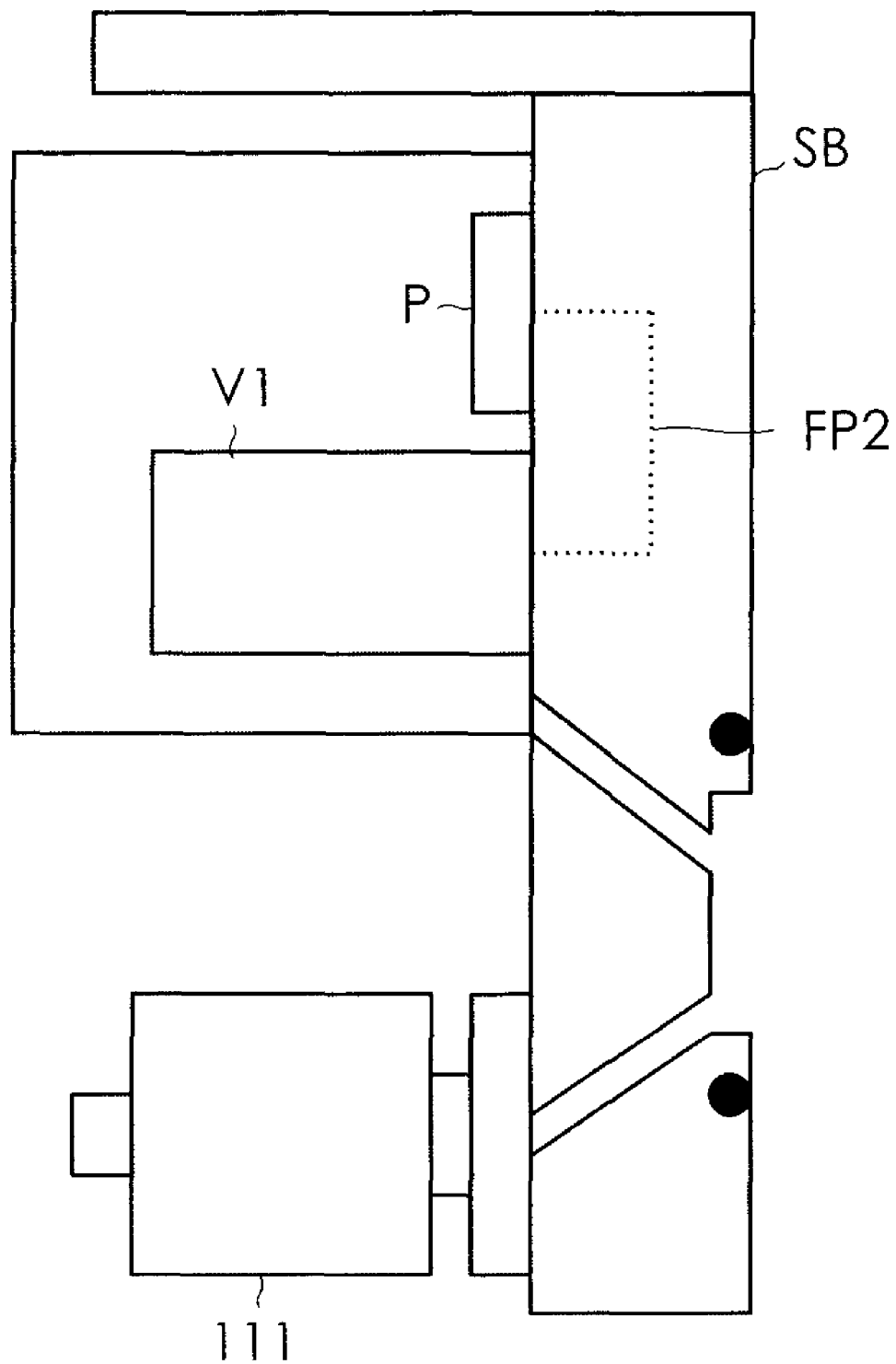

FIGS. 8A and 8B are a plan view and a right side view, respectively, of an example of a unit (an acrylic manifold) obtained by mounting the first and second switching valves V1 and V2, the circulation pump P, and a main portion of a salinity and temperature measurement sensor 111 on a single insulating resin substrate SB. The insulating resin substrate SB is formed by a transparent insulating resin substrate. In the example, an acrylic substrate is used as the insulating resin substrate. The pH indicator solution supply path FP0, the pH indicator solution discharge path FP6, and at least a part (FP1, FP2, FP3, and FP5) of the pH indicator circulation path 103C are formed in the insulating resin substrate SB by drilling. By adopting such a unitary structure (acrylic manifold), the number of pipes and the number of connectors necessary to form the pH indicator solution supply path FP0, the pH indicator solution discharge path FP6, and the pH indicator circulation path 103C can be reduced to reduce the number of locations where a leakage possibly occurs. Thus, the structure of the measurement apparatus can be simplified.

INDUSTRIAL APPLICABILITY

According to the present invention, pH measurement values can be corrected using the change rate $\Delta A_0$ of the isosbestic point absorbance even if a new substance generated by deterioration and decomposition of the pH indicator absorbs light at two peak absorption wavelengths, namely the first and second peak absorption wavelengths $\lambda_1$ and $\lambda_2$. Thus, the measurement accuracy can be enhanced compared to the related art. According to the present invention, in addition, measurement can advantageously be performed also with a pH indicator whose basic spectrum and acid spectrum overlap each other at two peak wavelengths.

What is claimed is:
1. An apparatus for measuring a concentration of carbon dioxide in water, comprising:
   a measurement cell including a carbon dioxide permeable section that allows permeation of carbon dioxide but that does not allow permeation of water when the measurement cell is immersed in water;
   a pH indicator solution with which the measurement cell is filled and which changes in color in accordance with changes in pH, the pH indicator solution having a carbon dioxide concentration that finally becomes equal to the concentration of carbon dioxide in water, and the pH indicator solution establishing an equilibrium of:

 [Chemical formula 7]

if the pH indicator solution is represented as $H_2L$;
   a spectrum measuring apparatus that measures an absorption spectrum of light absorbed by the pH indicator solution;
   an absorbance computing section that computes from the absorption spectrum a first absorbance $A_1$ at a first peak absorption wavelength $\lambda_1$ which is equivalent to a concentration of the $HL^-$ in the pH indicator solution, a second absorbance $A_2$ at a second peak absorption wavelength $\lambda_2$ which is equivalent to a concentration of the $L^{2-}$ in the pH indicator solution, an isosbestic point absorbance $A_0$ at an isosbestic point wavelength $\lambda_0$ at which the pH indicator solution does not show changes in absorbance in accordance with changes in pH, and a non-light-absorbing absorbance $A_b$ at a non-light-absorbing wavelength $\lambda_b$;

a pH value computing section that computes a pH value of the pH indicator solution using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$;

a carbon dioxide concentration determining section that determines the concentration of carbon dioxide in water from the computed pH value; and a deterioration determining section that computes a change rate $\Delta A_0$ of the isosbestic point absorbance $A_0$ and determines that the pH indicator solution is deteriorated when the change rate $\Delta A_0$ is reduced by a predetermined reduction rate or more, wherein after the deterioration determining section determines deterioration of the pH indicator solution, the pH value computing section computes the pH value of the pH indicator solution using a corrected pH computation expression for correcting a deterioration of the pH value of the pH indicator solution on the basis of the change rate $\Delta A_0$.

2. The apparatus for measuring a concentration of carbon dioxide in water according to claim 1, wherein the basic pH computation expression is given by the following expression:

$$\text{pH} = pKa + \log\left(\frac{(A_2 - A_b)/(A_1 - A_b) - \varepsilon_{21}/\varepsilon_{11}}{\varepsilon_{22}/\varepsilon_{11} - (A_2 - A_b)/(A_1 - A_b)(\varepsilon_{12}/\varepsilon_{11})}\right) \quad \text{[Expression 5]}$$

where pKa is a dissociation constant of the pH indicator solution, $\varepsilon_{11}$ and $\varepsilon_{12}$ are respective molar absorption coefficients of $HL^-$ and $L^{2-}$ at the first peak absorption wavelength $\lambda_1$, and $\varepsilon_{21}$ and $\varepsilon_{22}$ are respective molar absorption coefficients of $HL^-$ and $L^{2-}$ at the second peak absorption wavelength $\lambda_2$; and the corrected pH computation expression is given by the following expression:

$$\text{pH} = pKa + \log\left(\frac{(A_2 - (1-\Delta A_0)B_2 - A_b)/}{(A_1 - (1-\Delta A_0)B_1 - A_b) - \varepsilon_{21}/\varepsilon_{11}} \middle/ \frac{\varepsilon_{22}/\varepsilon_{11} - (A_2 - (1-\Delta A_0)B_2 - A_b)/}{(A_1 - (1-\Delta A_0)B_1 - A_b) \times (\varepsilon_{12}/\varepsilon_{11})}\right) \quad \text{[Expression 6]}$$

where $\Delta A_0$ is the change rate of the isosbestic point absorbance, and $B_1$ and $B_2$ are respective absorbances of an indicator decomposition substance at the first and second peak absorption wavelengths $\lambda_1$ and $\lambda_2$.

3. The apparatus for measuring a concentration of carbon dioxide in water according claim 1, further comprising:

a first alarm signal generating section that determines that an abnormality is occurring to generate an alarm signal if the non-light-absorbing absorbance $A_b$ is reduced by a predetermined reduction rate or more with reference to an initial value.

4. The apparatus for measuring a concentration of carbon dioxide in water according to claim 1, wherein the spectrum measuring apparatus includes a light source that emits measurement light to the measurement cell, a light receiving element that receives the measurement light which has passed inside the measurement cell, and a measuring section that measures the absorption spectrum on the basis of an output of the light receiving element.

5. The apparatus for measuring a concentration of carbon dioxide in water according to claim 4, further comprising:

a second alarm signal generating section that generates an alarm signal indicating that an abnormality is occurring in the light source or the light receiving element if an output of the light source or the output of the light receiving element is reduced by a predetermined reduction rate or more with reference to an initial value.

6. The apparatus for measuring a concentration of carbon dioxide in water according to claim 4, further comprising:

a third alarm signal generating section that determines that an abnormality is occurring in the pH indicator solution in the measurement cell to generate an alarm signal if the non-light-absorbing absorbance $A_b$ is varied by a predetermined variation rate or more with reference to an initial value and an output of the light source or the output of the light receiving element is not varied by a predetermined variation rate or more with reference to an initial value.

7. The apparatus for measuring a concentration of carbon dioxide in water according to claim 1, further comprising:

a change command generating section that generates a change command requesting a change of the pH indicator solution in the measurement cell; and an indicator solution changer that changes the pH indicator solution in the measurement cell when the change command is input.

8. The apparatus for measuring a concentration of carbon dioxide in water according to claim 1, wherein the spectrum measuring apparatus includes a light source that emits measurement light to the measurement cell, a light receiving element that receives the measurement light which has passed through a light permeable section in the measurement cell, and a measuring section that measures the absorption spectrum on the basis of an output of the light receiving element;

the apparatus further comprises:

a first alarm signal generating section that determines that an abnormality is occurring to generate an alarm signal if the non-light-absorbing absorbance $A_b$ is varied by a predetermined variation rate or more with reference to an initial value, and a second alarm signal generating section that generates an alarm signal indicating that an abnormality is occurring in the light source or the light receiving element if an output of the light source or the output of the light receiving element is varied by a predetermined variation rate or more with reference to an initial value; and the deterioration determining section determines that the pH indicator solution is deteriorated when the alarm signal is not input from either of the first alarm signal generating section or the second alarm signal generating section.

9. The apparatus for measuring a concentration of carbon dioxide in water according to claim 4, wherein the light source is formed by a plurality of types of light emitting diodes with different wavelengths determined to allow measurement of the four wavelengths $\lambda_1$, $\lambda_2$, $\lambda_0$, and $\lambda_b$.

10. The apparatus for measuring a concentration of carbon dioxide in water according to claim 7, wherein the measurement cell and the indicator solution changer are configured to form a pH indicator circulation path that allows circulation of the pH indicator solution through the carbon dioxide permeable section during measurement performed by the spectrum measuring apparatus, and to discharge the pH indicator solution in the pH indicator circulation path from the pH indicator circulation path and fill the pH indicator circulation path with a new pH indicator solution when the change command is input.

11. The apparatus for measuring a concentration of carbon dioxide in water according to claim 10,
wherein the measurement cell includes the carbon dioxide permeable section, a light permeable section that allows permeation of the light, and a circulation pump, all of which are disposed in the pH indicator circulation path; and
the indicator solution changer includes a first switching valve disposed at a connection portion between a pH indicator solution supply path and the pH indicator circulation path and a second switching valve disposed at a connection portion between a pH indicator solution discharge path and the pH indicator circulation path, and operates the first and second switching valves to bring the pH indicator circulation path into a closed state by separating the pH indicator solution supply path and the pH indicator solution discharge path from the pH indicator circulation path during measurement, and to temporarily bring the pH indicator circulation path into an open state by connecting the pH indicator solution supply path and the pH indicator solution discharge path to the pH indicator circulation path and then bring the pH indicator circulation path back into the closed state when the change command is input.

12. The apparatus for measuring a concentration of carbon dioxide in water according to claim 11,
wherein at least the first and second switching valves and the circulation pump are mounted on a single insulating resin substrate, and the pH indicator solution supply path, the pH indicator solution discharge path, and at least a part of the pH indicator circulation path are formed in the insulating resin substrate by drilling.

13. A method for measuring a concentration of carbon dioxide in water, comprising the steps of:
immersing in water a measurement cell including a carbon dioxide permeable section that allows permeation of carbon dioxide but that does not allow permeation of water, the measurement cell being filled with a pH indicator solution that changes in color in accordance with changes in pH, the pH indicator solution having a carbon dioxide concentration that finally becomes equal to the concentration of carbon dioxide in water, and the pH indicator solution establishing an equilibrium of:

  [Chemical formula 8]

if the pH indicator solution is represented as $H_2L$;
measuring an absorption spectrum of light absorbed by the pH indicator solution;
computing from the absorption spectrum a first absorbance $A_1$ at a first peak absorption wavelength $\lambda_1$ which is equivalent to a concentration of $HL^-$ in the pH indicator solution, a second absorbance $A_2$ at a second peak absorption wavelength $\lambda_2$ which is equivalent to a concentration of $L^{2-}$ in the pH indicator solution, an isosbestic point absorbance $A_0$ at an isosbestic point wavelength at which the pH indicator solution does not show changes in absorbance in accordance with changes in pH in the pH indicator solution, and a non-light-absorbing absorbance $A_b$ at a non-light-absorbing wavelength $\lambda_b$;
computing a pH value of the pH indicator solution using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$;
determining the concentration of carbon dioxide in water from the computed pH value;
computing a change rate $\Delta A_0$ of the isosbestic point absorbance $A_0$ and determining that the pH indicator solution is deteriorated when the change rate $\Delta A_0$ is reduced by a predetermined reduction rate or more; and
after deterioration of the pH indicator solution is determined, computing the pH value of the pH indicator solution using a corrected pH computation expression for correcting a deterioration of the pH value of the pH indicator solution on the basis of the change rate $\Delta A_0$ of the isosbestic point absorbance $A_0$.

14. The method for measuring a concentration of carbon dioxide in water according to claim 13,
wherein the basic pH computation expression is given by the following expression:

$$pH = pKa + \log\left(\frac{(A_2-A_b)/(A_1-A_b)-\varepsilon_{21}/\varepsilon_{11}}{\varepsilon_{22}/\varepsilon_{11}-(A_2-A_b)/(A_1-A_b)(\varepsilon_{12}/\varepsilon_{11})}\right) \quad \text{[Expression 7]}$$

where, when the pH indicator solution establishes an equilibrium of:

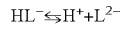  [Chemical formula 9]

if the pH indicator solution is represented as $H_2L$, pKa is a dissociation constant of the pH indicator solution, $\varepsilon_{11}$ and $\varepsilon_{12}$ are respective molar absorption coefficients of $HL^-$ and $L^{2-}$ at the first peak absorption wavelength $\lambda_1$, and $\varepsilon_{21}$ and $\varepsilon_{22}$ are respective molar absorption coefficients of $HL^-$ and $L^{2-}$ at the second peak absorption wavelength $\lambda_2$; and
the corrected pH computation expression is given by the following expression:

$$pH = pKa + \log\left(\frac{(A_2-(1-\Delta A_0)B_2-A_b)/}{(A_1-(1-\Delta A_0)B_1-A_b)-\varepsilon_{21}/\varepsilon_{11}}{\varepsilon_{22}/\varepsilon_{11}-(A_2-(1-\Delta A_0)B_2-A_b)/}{(A_1-(1-\Delta A_0)B_1-A_b)\times(\varepsilon_{12}/\varepsilon_{11})}\right) \quad \text{[Expression 8]}$$

where $\Delta A_0$ is the change rate of the isosbestic point absorbance, and $B_1$ and $B_2$ are respective absorbances of an indicator decomposition substance at the first and second peak absorption wavelengths $\lambda_1$ and $\lambda_2$.

15. The method for measuring a concentration of carbon dioxide in water according to claim 13, further comprising the step of:
determining that an abnormality is occurring to generate an alarm signal if the non-light-absorbing absorbance $A_b$ is varied by a predetermined variation rate or more with reference to an initial value.

16. The method for measuring a concentration of carbon dioxide in water according to claim 13, further comprising the steps of:
providing a light source that emits light to a light permeable section of the measurement cell and a light receiving element that receives the light which has passed through the light permeable section; and generating an alarm signal indicating that an abnormality is occurring in the light source or the light receiving element if an output of the light source or an output of the light receiving element is varied by a predetermined variation rate or more with reference to an initial value.

17. The method for measuring a concentration of carbon dioxide in water according to claim 13, further comprising the steps of:

providing a light source that emits light to the measurement cell and a light receiving element that receives the light which has passed inside the measurement cell; and determining that an abnormality is occurring in the pH indicator solution in the measurement cell to generate an alarm signal if the non-light-absorbing absorbance $A_b$ is varied by a predetermined variation rate or more with reference to an initial value and an output of the light source or an output of the light receiving element is not varied by a predetermined variation rate or more with reference to an initial value.

18. The method for measuring a concentration of carbon dioxide in water according to claim 17, further comprising the step of:

generating a change command requesting a change of the pH indicator solution in the measurement cell when the alarm signal is generated.

19. The method for measuring a concentration of carbon dioxide in water according to claim 16, further comprising the step of:

suspending measurement of the carbon dioxide concentration when the alarm signal is generated.

20. The method for measuring a concentration of carbon dioxide in water according to claim 13, further comprising the steps of:

providing a light source that emits light to a light permeable section of the measurement cell and a light receiving element that receives the light which has passed through the light permeable section; and determining that the pH indicator solution is deteriorated if the non-light-absorbing absorbance $A_b$ is not varied by a predetermined variation rate or more with reference to an initial value, an output of the light source or an output of the light receiving element is not varied by a predetermined variation rate or more with reference to an initial value, and the isosbestic point absorbance $A_0$ is varied by a predetermined variation rate or more with reference to an initial value.

21. A method for measuring a concentration of carbon dioxide in water, comprising the steps of:

immersing in water a measurement cell including a carbon dioxide permeable section that allows permeation of carbon dioxide but that does not allow permeation of water, the measurement cell being filled with a pH indicator solution that changes in color in accordance with changes in pH, the pH indicator solution having a carbon dioxide concentration that finally becomes equal to the concentration of carbon dioxide in water, and the pH indicator solution establishing an equilibrium of:

 [Chemical formula 10]

if the pH indicator solution is represented as $H_2L$;

measuring an absorption spectrum of light absorbed by the pH indicator solution;

computing from the absorption spectrum a first absorbance $A_1$ at a first peak absorption wavelength $\lambda_1$ which is equivalent to a concentration of $HL^-$ in the pH indicator solution, a second absorbance $A_2$ at a second peak absorption wavelength $\lambda_2$ which is equivalent to a concentration of $L^{2-}$ in the pH indicator solution, an isosbestic point absorbance $A_0$ at an isosbestic point wavelength at which the pH indicator solution does not show changes in absorbance in accordance with changes in pH in the pH indicator solution, and a non-light-absorbing absorbance $A_b$ at a non-light-absorbing wavelength $\lambda_b$;

computing a pH value of the pH indicator solution using a basic pH computation expression for computing the pH value of the pH indicator solution on the basis of a ratio $(A_1-A_b)/(A_2-A_b)$ of a difference $(A_1-A_b)$ between the first absorbance $A_1$ and the non-light-absorbing absorbance $A_b$ to a difference $(A_2-A_b)$ between the second absorbance $A_2$ and the non-light-absorbing absorbance $A_b$;

determining the concentration of carbon dioxide in water from the computed pH value; and computing a change rate $\Delta A_0$ of the isosbestic point absorbance $A_0$ and determining that the pH indicator solution is deteriorated when the change rate $\Delta A_0$ is reduced by a predetermined reduction rate or more.

* * * * *